United States Patent

Arenson et al.

[11] Patent Number: 5,899,864
[45] Date of Patent: May 4, 1999

[54] ADAPTIVE TEMPORAL FILTERING TO ENHANCE FLUID FLOW OR TISSUE MOTION IMAGING

[75] Inventors: James W. Arenson, Woodside, Calif.; Stanley S. C. Chim, Oakcreek, Wis.; Ismayil M. Guracar, Redwood City; Samuel H. Maslak, Woodside, both of Calif.

[73] Assignee: Acuson Corporation, Mountain View, Calif.

[21] Appl. No.: 08/827,863

[22] Filed: Apr. 9, 1997

Related U.S. Application Data

[63] Continuation of application No. 08/366,803, Dec. 30, 1994, abandoned.

[51] Int. Cl.⁶ .................................. A61B 8/00; A61B 8/06
[52] U.S. Cl. ............................................. 600/455; 600/453
[58] Field of Search .................................. 600/443, 447, 600/455, 441

[56] References Cited

U.S. PATENT DOCUMENTS

| | | | |
|---|---|---|---|
| 4,751,846 | 6/1988 | Dousse | 73/602 |
| 4,785,818 | 11/1988 | Hardin | 600/443 |
| 4,887,306 | 12/1989 | Hwang et al. | 382/261 |
| 4,928,698 | 5/1990 | Bonnefons | 600/455 |
| 5,014,710 | 5/1991 | Maslak et al. | 600/441 |
| 5,099,848 | 3/1992 | Parker et al. | 600/443 |
| 5,152,292 | 10/1992 | Karp | 128/661.08 |
| 5,165,413 | 11/1992 | Maslak et al. | 600/441 |
| 5,215,094 | 6/1993 | Franklin et al. | 128/661.08 |
| 5,228,009 | 7/1993 | Forestieri et al. | 128/661.09 X |
| 5,285,788 | 2/1994 | Arenson et al. | 600/441 |
| 5,299,174 | 3/1994 | Forestieri et al. | 128/661.09 X |
| 5,349,524 | 9/1994 | Daft et al. | 600/454 X |
| 5,357,465 | 10/1994 | Hall et al. | 600/454 |
| 5,357,580 | 10/1994 | Forestieri et al. | 382/6 |
| 5,363,849 | 11/1994 | Suorsa et al. | 600/454 |
| 5,394,874 | 3/1995 | Forestieri et al. | 128/660.05 |
| 5,413,105 | 5/1995 | Forestieri | 128/660.05 |
| 5,429,137 | 7/1995 | Phelps et al. | 600/455 |
| 5,450,216 | 9/1995 | Kasson | 358/518 |
| 5,467,770 | 11/1995 | Smith et al. | 128/661.08 |
| 5,487,389 | 1/1996 | Benjamin et al. | 600/455 |
| 5,494,037 | 2/1996 | Benjamin et al. | 600/455 |
| 5,515,852 | 5/1996 | Karp et al. | 128/660.07 |

OTHER PUBLICATIONS

Kasai, C. et al Real–Time 2D BF Imaging Using An Autocorrelation Technique, IEEE SIUS vol. SU–32 No. 3 pp. 458–464 May 1985.

Evans, D.M et al "Real–Time CFM Systems", Doppler–UTS–Physics, Instrumentation & Clin Appln, Wiley & Sons N.Y. pp. 102–105 (1989).

Bonneforus, O. et al "TD Formulation of PD UTS & BV Estimation by Cross–Correlation", VTS Imaging 8, 73–75 (1986).

Van Leuwen et al, Simulation of Real–Time Freq. Est. for Pulsed Doppler Systems, UTS Imaging 8, 252–271 (1986).

"Real–Time Two–Dimensional Blood Flow Imaging Using an Autocorrelation Technique," by Kasai et al., IEEE transactions on Sonics and Ultrasonics, vol. SU–32, No. 3, May 1985.

"Time Domain Formulation of Pulse Doppler Ultrasound and Blood Velocity Estimation by Cross–Correlation," by Bonnefous et al., Ultrasonic Imaging, 8, pp. 73–85 (1986).

*Primary Examiner*—Francis J. Jaworski
*Attorney, Agent, or Firm*—Brinks Hofer Gilson & Lione

[57] ABSTRACT

The energy, power or amplitude of Doppler or time shift information signals is compared to a threshold in order to select a large or small weighting factor for temporal persistence. In the event of a "flash" signal or strong arterial flow signal, a small weighting factor is chosen to reduce the extent of temporal persistence via feedback of the averaged value for the prior frames so that the effect of the "flash" or strong flow signal would quickly dissipate in the imaging of subsequent frames and good temporal resolution preserved for the current frames, while low energy flow signals would cause a large weighting factor to be selected to improve the signal-to-noise ratio of low energy signals. Similar effects can be achieved by clipping the signals to not exceed a certain threshold.

50 Claims, 6 Drawing Sheets

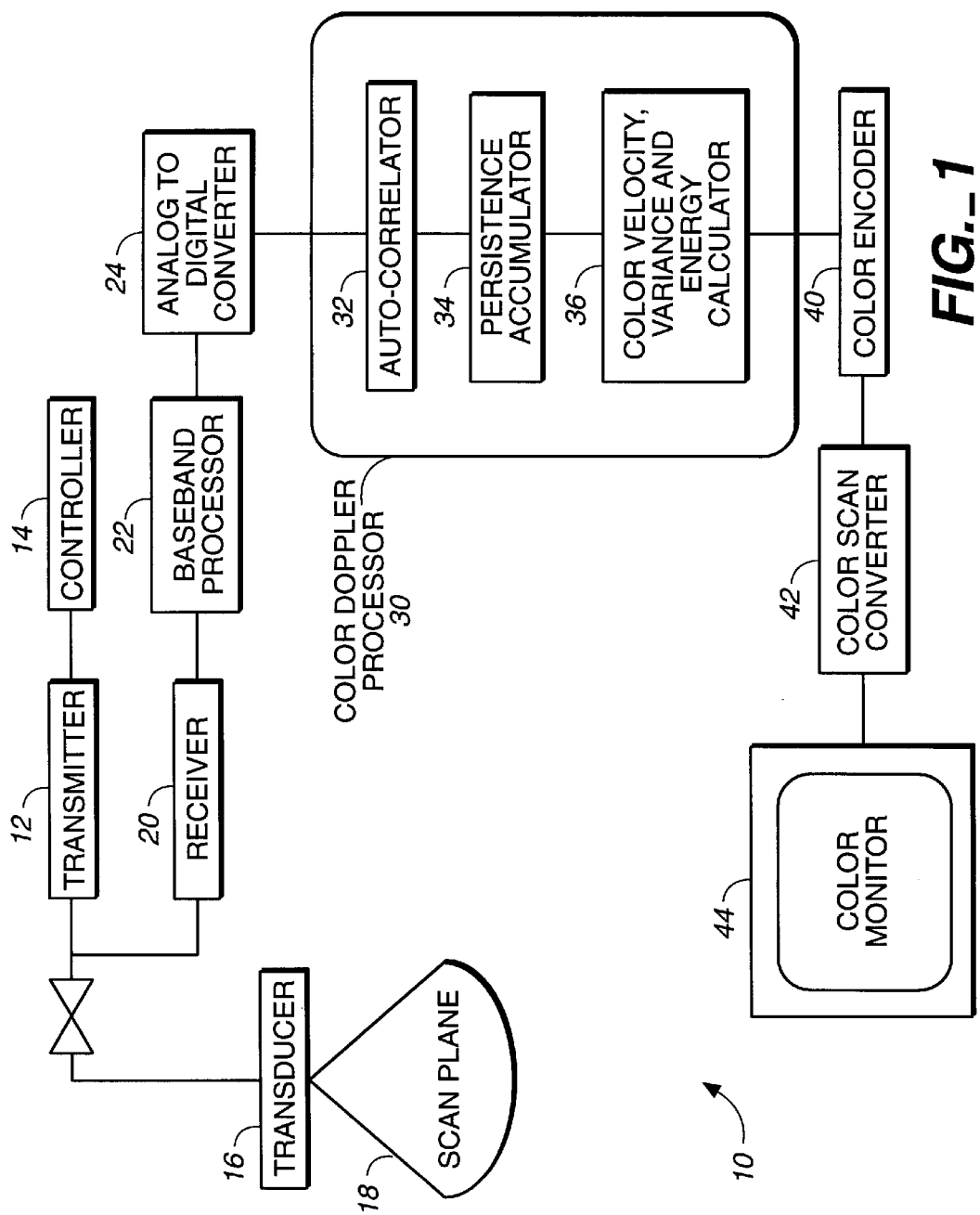

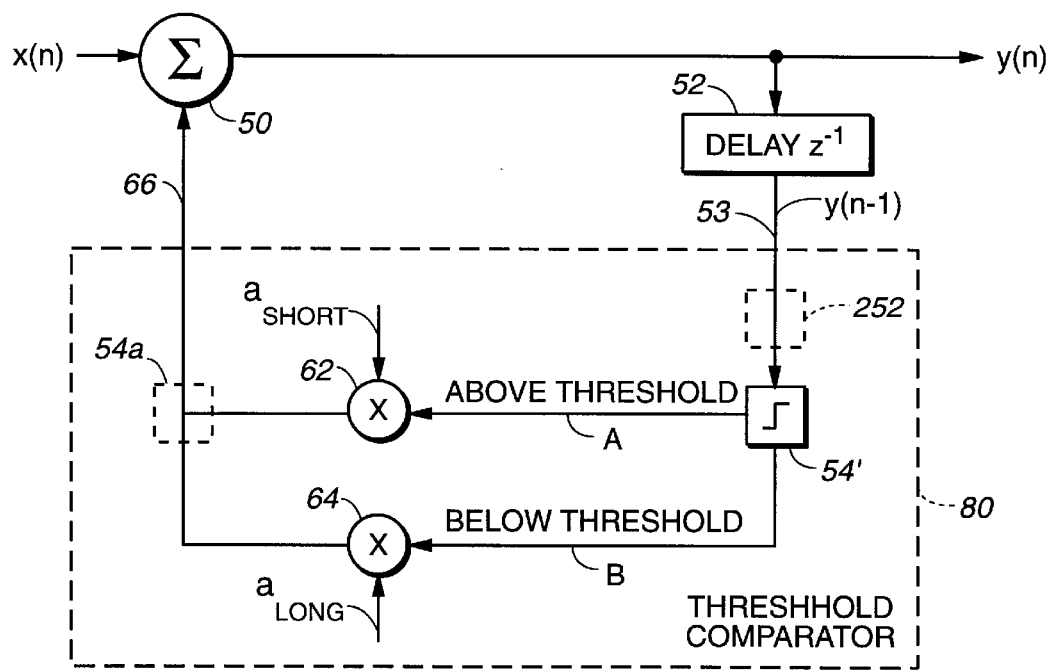
FIG._2A
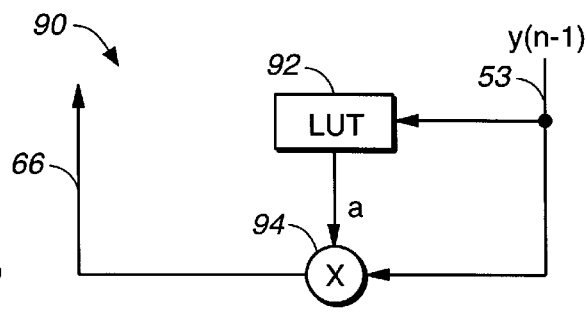
FIG._2B

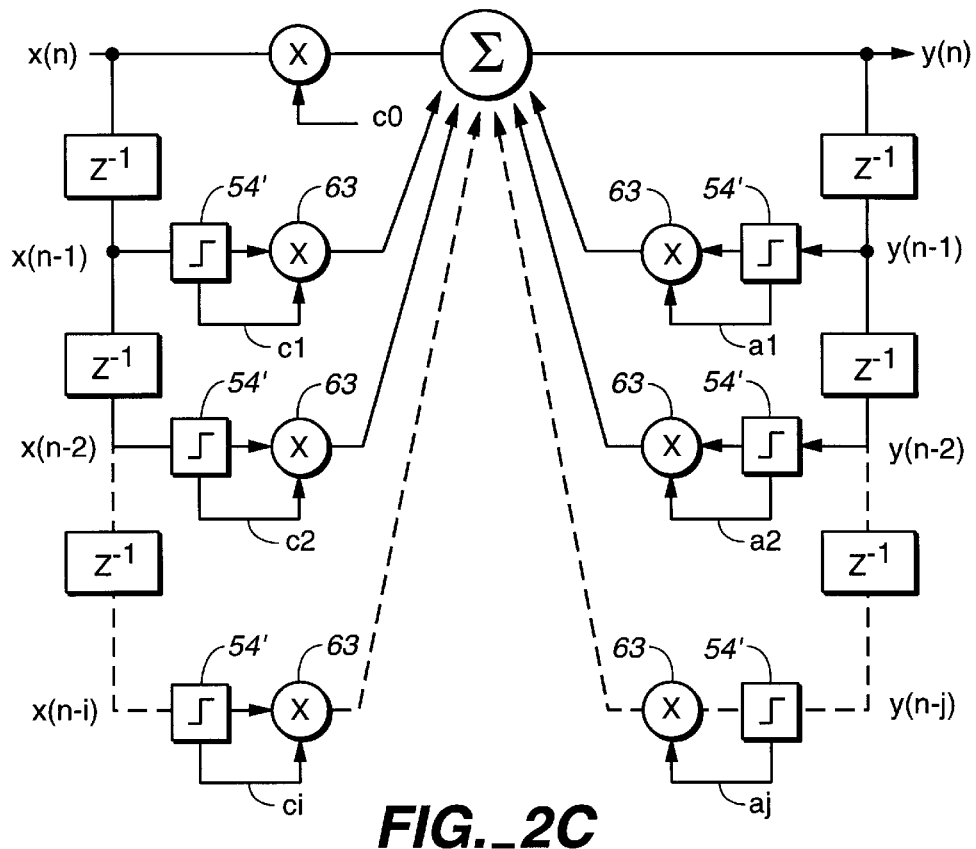
FIG._2C
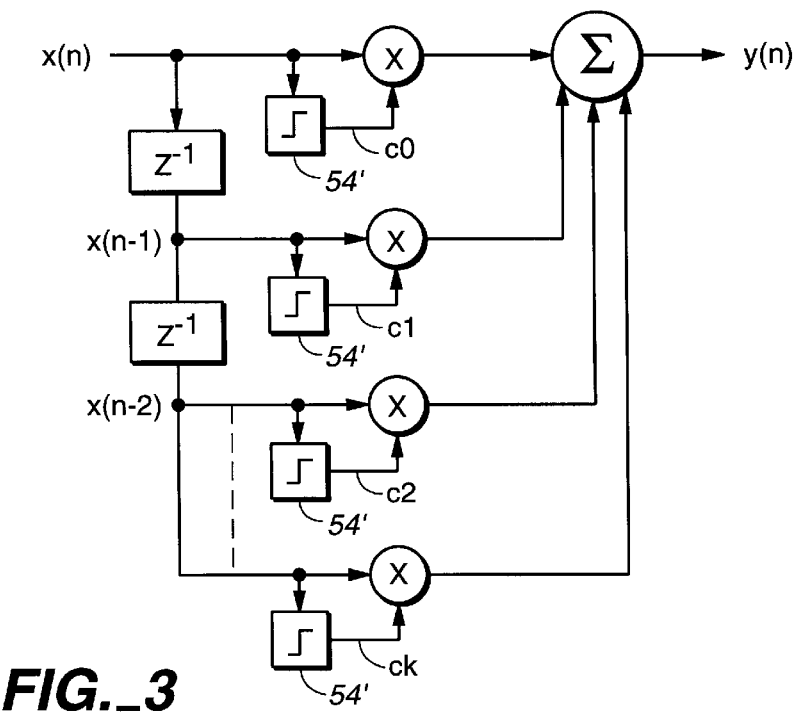
FIG._3

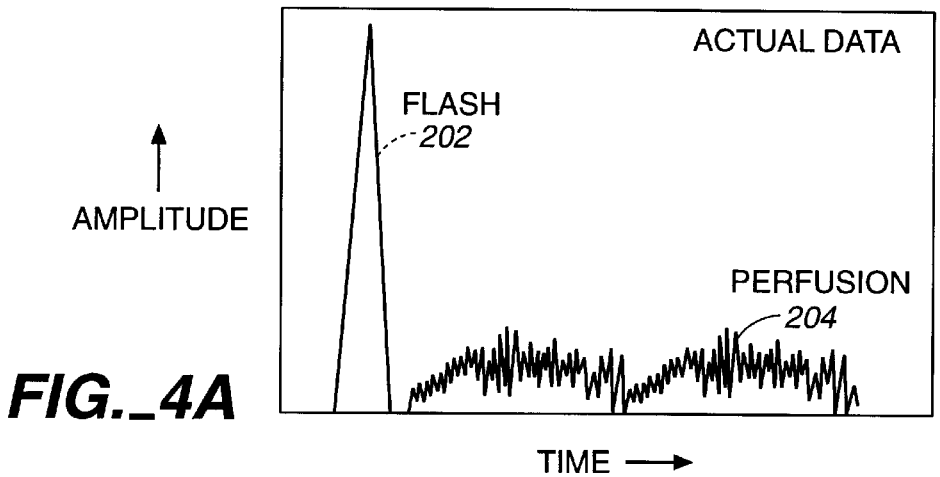
FIG._4A
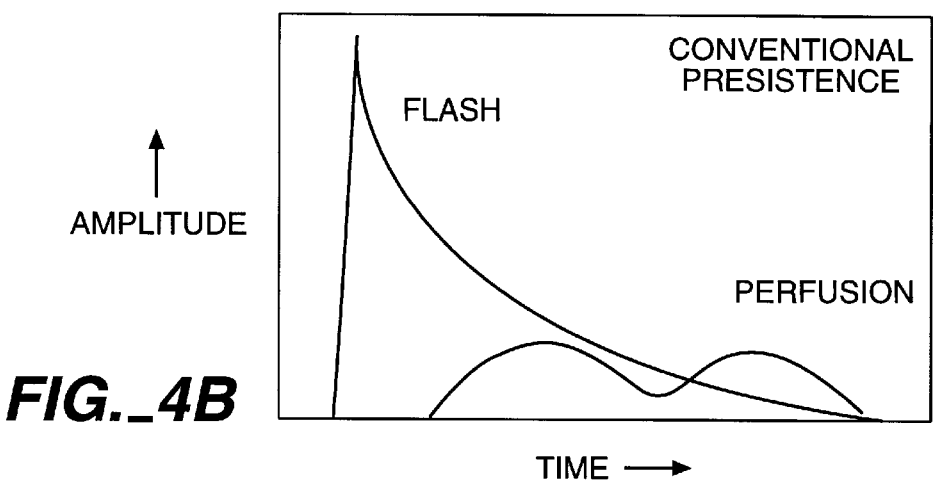
FIG._4B
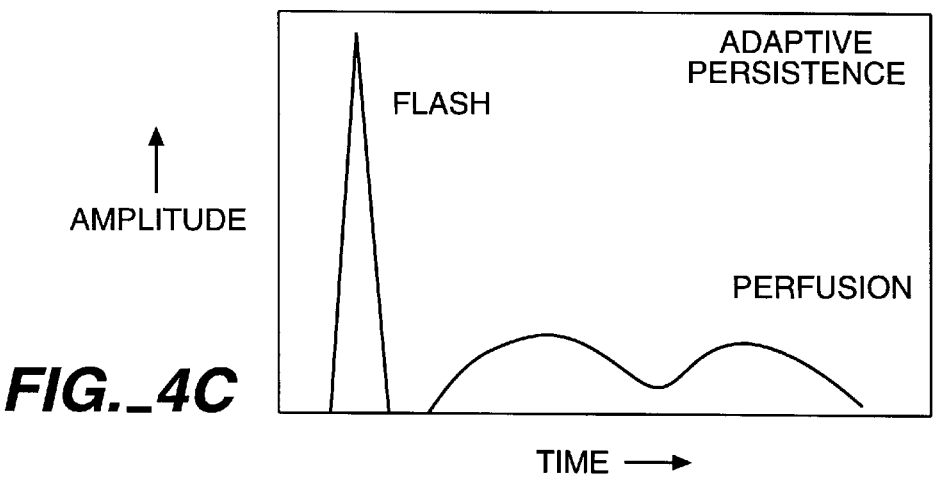
FIG._4C

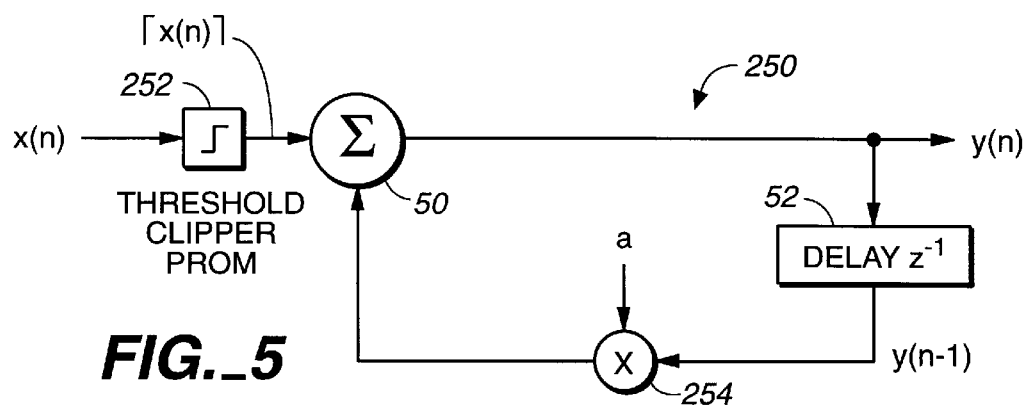
FIG._5
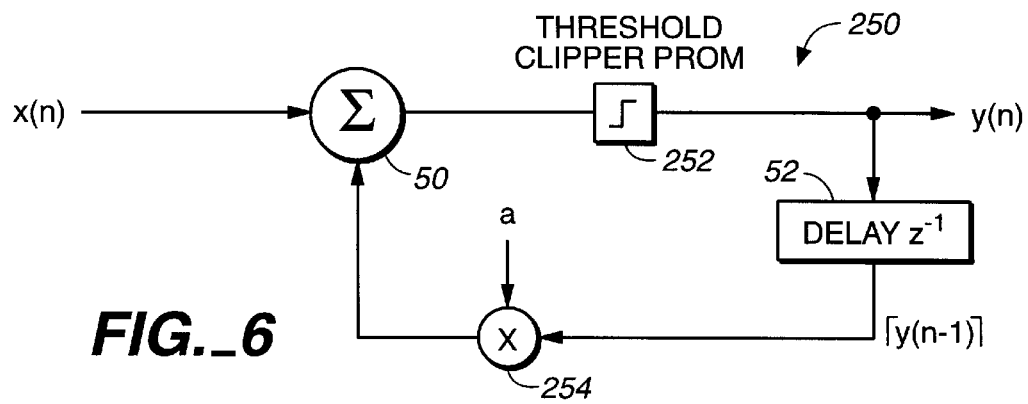
FIG._6
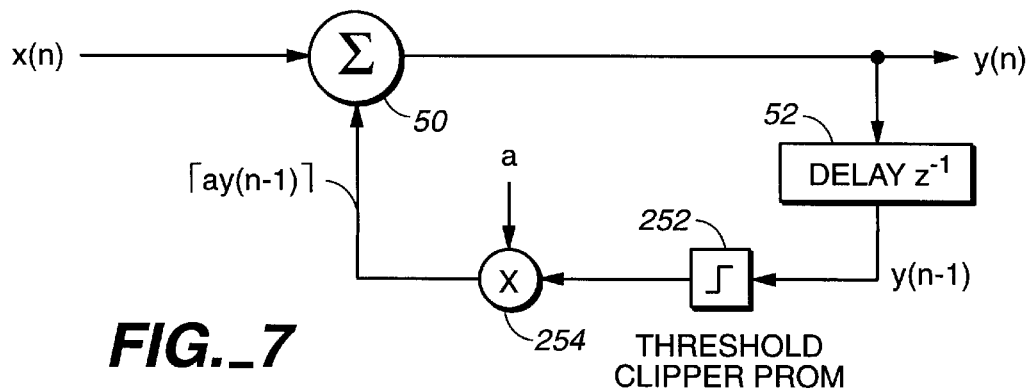
FIG._7

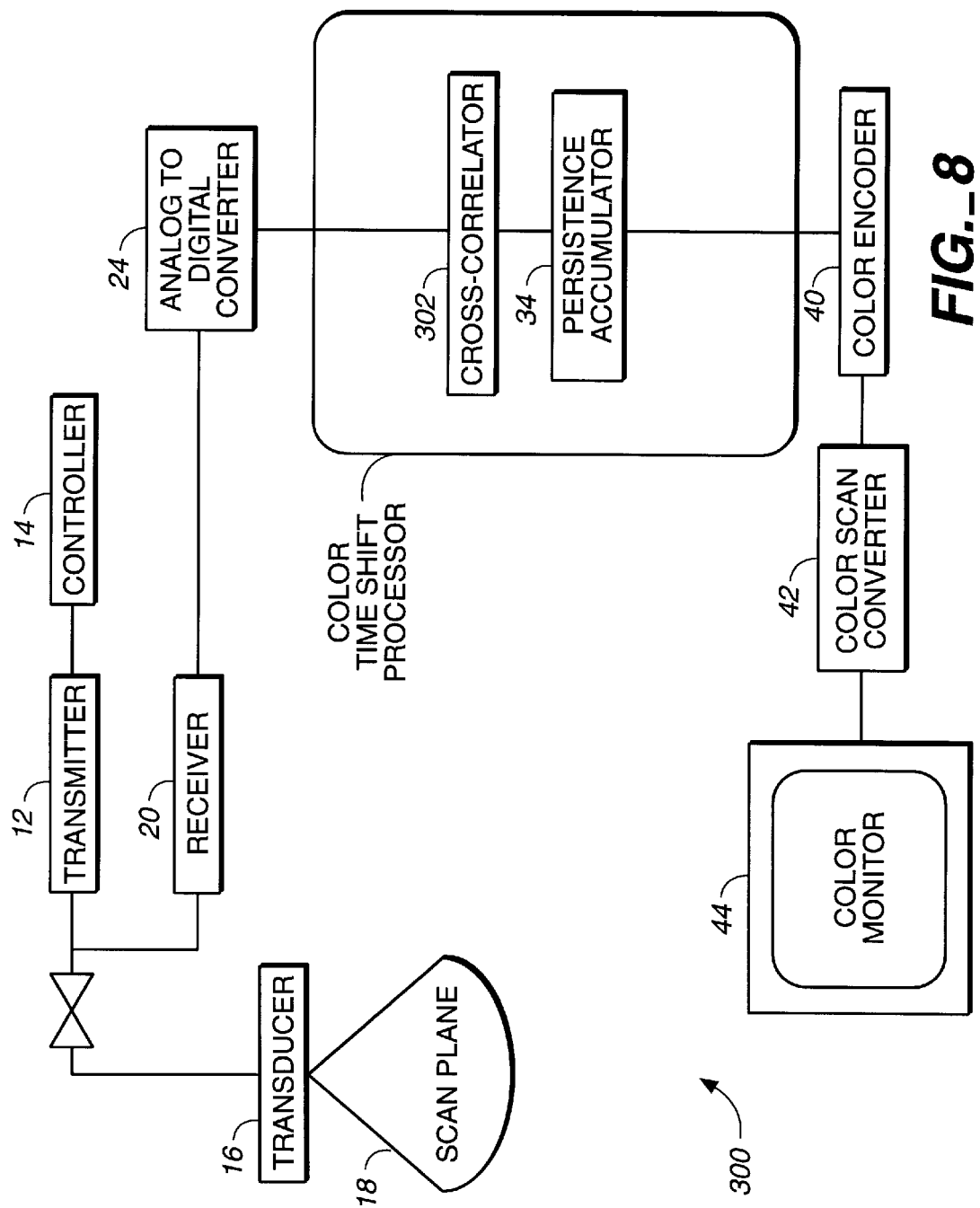
FIG._8

ADAPTIVE TEMPORAL FILTERING TO ENHANCE FLUID FLOW OR TISSUE MOTION IMAGING

This application is a continuation, of application Ser. No. 08/366,803, filed Dec. 30, 1994 abandoned.

BACKGROUND OF THE INVENTION

This invention relates in general to ultrasound diagnostic imaging systems, and in particular, to an adaptive temporal filtering system for enhancing Doppler or time shift signal data.

In conventional color Doppler imaging, an ultrasound system (such as the Acuson XP) derives indices of moving targets inside a body from the received Doppler signals. For example, mean velocity, acceleration, energy and standard deviation (or velocity variance) can be measured from either moving blood cells or moving myocardium or other tissues. These indices are estimated from the received Doppler signal. As with all physical measurements, the estimates include random variations or noise.

In order to reduce the random noise, multiple Doppler samples are acquired and averaged together. By averaging these samples, the random noise tends to cancel out, while the real underlying signals tend to be reinforced, thereby improving the signal-to-noise ratio (SNR). Since the samples are taken sequentially in time, this averaging operation is equivalent to temporal integration of the sampled Doppler signal. Temporal integration, also commonly referred to as persistence, is important for good color Doppler performance since it improves the sensitivity of the system and allows users to detect the very smallest of Doppler signals. While the increase in SNR is important for the conventional color Doppler velocity imaging mode, it is especially important for the more recent color Doppler energy imaging mode where the goal is to detect the very smallest blood flow and perfusion signals.

Typically, temporal integration takes the current Doppler sample containing blood flow information at a location in the body and sums it with a specified number of previous Doppler samples containing blood flow information at the same location in the body at previous times. Sometimes these previous Doppler samples can be "weighted" so that the oldest Doppler samples contribute least to the integrated value. The amount of persistence is a user selectable parameter, and varies either the number of previous Doppler samples included in the integration or the weighting of the previous Doppler samples. In a typical approach, the current persistence function was implemented using a feedback circuit for an input data sequence x(n), the persisted data y(n) may be described by:

$$y(n)=x(n)+a^*y(n-1)$$

where a is a fixed constant selected by the user according to the degree of persistence desired, and n is the sample number.

The old (conventional) temporal integration process is applied uniformly to all received Doppler signals irrespective of other factors such as, for example, their strength. Therefore, as persistence is increased, all aspects of the color Doppler signal are persisted. Here, both weak and strong signals are persisted in the same way. Following are cases illustrating the shortcomings.

First, when a physician moves and re-positions a transducer or when a patient breathes or moves in a clinical environment, very high amplitude Doppler signals are produced from transducer or tissue movements. Additionally, pulsations from the cardiovascular system propagate throughout the body, producing motion artifacts in most tissues. These types of motions create echo amplitudes that are many times greater than those from the weak blood flow signals. The result is color "flash" artifact, where large swaths of color appear on the video display and obscure any low level Doppler signals of interest.

The "flash" artifact is further accentuated by temporal averaging. While the pulse of moving tissue may be of short duration, it will be stretched out in time by the integration process. The old temporal integration process is unable to discriminate against this "flash" artifact and will thus temporally integrate (or persist) the "flash" artifact as long or longer than the blood signal. The long duration of this color "flash" obscures normal scanning and slows down the scanning procedure.

A long temporal integration (or persistence) is often preferred when the clinical user needs to distinguish weak blood perfusion from background noise. However, there are also flow states where the temporal characteristics of the Doppler signal are important, for example, in differentiating steady venous flow from pulsatile arterial flow. There are times when both of these flow conditions occur in the same image. A single persistence cannot be optimized for both of these conditions.

There are also imaging conditions where both good sensitivity and good temporal resolution are required along with reduced "flash" artifact. With the old persistence function, the clinician has to trade off temporal resolution and increased "flash" artifact for better sensitivity. For example, with an indiscriminate persistence process, the high velocity blood flow from a major blood vessel is temporally integrated the same amount as a weak perfusion signal from an adjacent tissue. If the persistence is set correctly for the major vessel flow, the weak perfusion signal may be buried in noise. Alternatively, if the persistence is set correctly for the weak perfusion signals, the high velocity blood flow will appear "sluggish" and its color Doppler representation is not physiological. Furthermore, any "flash" artifact will be persisted too long and could obscure the weak perfusion signals.

Generally, there may be cases where different aspects of the color Doppler signal should be persisted differently.

In view of the above problems of conventional methods, a number of approaches have been proposed. In U.S. Pat. No. 5,357,580, Forestieri et al. propose a temporal filtering scheme which computes a weighted temporal average of the current and previous blood flow velocities, employing weights that are functions of the blood flow velocities, so that imaging information for low velocities are heavily averaged while fast moving blood velocities are maintained with little or no averaging. The output of the system is then displayed in the velocity imaging mode. Velocity may not be the best parameter to use to determine the amount of persistence. Furthermore, velocity imaging is not as sensitive as color Doppler energy imaging, especially for sensing perfusion signals.

Another approach is disclosed in U.S. Pat. No. 5,152,292 to Karp, where the velocity and magnitude components of Doppler signals are compared to "flash" rejection levels, so as to reject and discard velocity components containing "flash" so that such components are not processed by color flow display circuitry. This approach does not adjust the persistence.

None of the above-described approaches is entirely satisfactory. It is therefore desirable to provide an improved temporal filtering system with enhanced characteristics.

SUMMARY OF THE INVENTION

The invention employs the following general scheme. A first sequence of Doppler information signals are acquired by sensing the echoes from fluid flow or tissue motion in a body of ultrasound signals transmitted sequentially towards the body. In the preferred embodiment, each signal in the first sequence conveys information on Doppler information from fluid flow or tissue motion at a location in a corresponding frame, and a subsequent signal in the first sequence conveys similar information at the same location in a subsequent corresponding frame. A second sequence of temporally filtered signals is then obtained from the first sequence by temporally persisting the signals in the first sequence and/or the signals in the second sequence, and is known as the second sequence of persisted signals corresponding to the first sequence. The signals in the second sequence contains information related to mean velocity, variance of velocity of the fluid flow or tissue motion and energy of the Doppler information signals. This invention is directed to a system for performing an averaging process to obtain signals in the second sequence as energy weighted averages of signals in the first sequence and/or the second sequence. This general scheme applies also to temporal filtering of time shift data as explained below.

The first sequence of Doppler information could be in the form of autocorrelation coefficients, or mean velocity, variance of velocity or energy estimates derived from these coefficients. Other representation of the Doppler signals could also be used. While the term "velocity" is used in this application, it should be understood that the quantity "velocity" processed here is derived from the Doppler frequency shift, and the mean frequency or wavelength estimate is converted to a mean velocity estimate by use of the well known Doppler equation:

$$V = f_D * c / 2 f_o * \cos\theta$$

where $f_D$ is the Doppler frequency shift, c is the speed of sound, $f_o$ is the transmitted frequency and $\theta$ is the Doppler angle or the angle subtended by the ultrasound beam and the direction of flow. Therefore, it will be understood that whenever "mean velocity" is referred to in the application, "mean frequency" or "mean wavelength" may be used instead; such variations are within the scope of the invention.

Instead of performing temporal averaging using the energy of the Doppler information or time shift signals, it is possible to perform the averaging using the power or the amplitudes of such signals instead; where power is the energy of such signals per unit time and amplitude is proportional to the square root of power. For simplicity, the term "energy related parameter" of a signal in this application will mean "energy" and/or "power" and/or "amplitude" of the signal and the last three terms in quotations are used interchangeably.

One aspect of the invention is directed towards an ultrasound diagnostic imaging method for imaging conditions of fluid flow or tissue motion within the body, comprising the step of providing a first time sequence of Doppler information signals containing Doppler information from the fluid flow or tissue motion. The method further comprises producing from said first time sequence of Doppler information signals a corresponding second time sequence of persisted signals. The producing step includes performing an averaging process to obtain at least one of said persisted signals as a weighted average of two or more of the Doppler information signals and/or the persisted signals and/or signals derived therefrom. The averaging process employs weighting factors that are functions of an energy related parameter of one or more Doppler information signals and/or the persisted signals and/or signals derived therefrom.

Another aspect of the invention is directed towards an ultrasound diagnostic imaging method which is the same as that described immediately above, except that instead of including the performance of an averaging process, the producing step includes the step of clipping the value of a combination of one or more Doppler information signals in the first sequence and/or the persisted signals in the second sequence and/or signals derived therefrom so that the value of the combination does not exceed a non-zero predetermined value.

Instead of producing the above-described first and second time sequences of signals from Doppler information, similar time sequences can be derived from time shift information instead. Thus, another aspect of the invention is directed towards an ultrasound diagnostic imaging method for imaging conditions of fluid flow or tissue motion within the body, comprising providing a first time sequence of information signals, each signal in the sequence containing time shift information from the fluid flow or tissue motion, and producing from said first time sequence of information signals a corresponding second time sequence of persisted signals. The producing step includes performing an averaging process to obtain at least one of said persisted signals as a weighted average of two or more of the information signals in the first sequence and/or the persisted signals in the second sequence and/or signals derived therefrom. The averaging process employs weighting factors that are functions of an energy related parameter of one or more information signals in the first sequence and/or the persisted signals in the second sequence and/or signals derived therefrom.

Another aspect of the invention is directed towards an ultrasound diagnostic imaging method similar to the one described immediately above employing time shift information, but where, instead of performing an averaging process in the producing step, the producing step includes the step of clipping the value of a combination of one or more information signals in the first sequence and/or the persisted signals in the second sequence and/or signals derived therefrom so that the value of the combination does not exceed a non-zero predetermined value.

Still another aspect of the invention is directed towards an ultrasound diagnostic imaging apparatus for imaging conditions of fluid flow or tissue motion within the body, comprising means for providing a first time sequence of Doppler information signals containing Doppler information from the fluid flow or tissue motion; and means for producing from said first time sequence of Doppler information signals a corresponding second time sequence of persisted signals. Said producing means includes means for performing an averaging process for obtaining at least one of said persisted signals as a weighted average of two or more of the Doppler information signals and/or the persisted signals and/or signals derived therefrom, employing weighting factors that are functions of an energy related parameter of one or more of the Doppler information signals in the first sequence and/or the persisted signals in the second sequence and/or signals derived therefrom.

Yet another aspect of the invention is directed towards an ultrasound diagnostic imaging apparatus similar to the apparatus described immediately above, but where, instead of including means for performing an averaging process, the producing means includes means for clipping the value of the combination of one or more of the Doppler information signals in the first sequence and/or the persisted signals in the second sequence and/or signals derived therefrom so that the combination does not exceed a non-zero predetermined value.

Again, as in the case of the method aspects of the invention, the above-described averaging process or clipping can be applied to time shift information instead of Doppler shift information. Thus yet another aspect of the invention is directed towards an ultrasound diagnostic image apparatus for imaging conditions of fluid flow or tissue motion within the body, comprising means for providing a first time sequence of information signals, each signal in the sequence containing time shift information from the fluid flow or tissue motion, and means for producing from said first time sequence of time shift information signals a corresponding second time sequence of persisted signals. The producing means includes means for performing an averaging process to obtain at least one of said persisted signals as a weighted average of two or more of the information signals and/or the persisted signals and/or signals derived therefrom, employing weighting factors that are functions of an energy related parameter of one or more of the information signals in the first sequence and/or the persisted signals in the second sequence and/or signals derived therefrom.

Still another aspect of the invention is directed towards an ultrasound diagnostic imaging apparatus similar to the one described immediately above, but where, instead of including means for performing an averaging process, the producing means includes means for clipping the value of a combination of one or more information signals in the first sequence and/or the persisted signals in the second sequence and/or signals derived therefrom so that such combination does not exceed a non-zero predetermined value.

Yet one more aspect of the invention is directed to an ultrasound diagnostic imaging method for imaging conditions of fluid flow or tissue motion within a body. The method includes the steps of providing a first sequence of information signals containing Doppler or time shift information from the fluid flow or tissue motion; and producing from said first sequence of Doppler information signals a corresponding second time sequence of persisted signals. The producing step includes analyzing one or a combination of one or more information signals and/or persisted signals and/or signals derived therefrom to determine whether said information signals indicate types of information present in the information signals, said types including noise, low energy flow or tissue motion, high energy flow or tissue motion or flash, and selecting one or more weighting factors according to the type or types of information present. The producing step also includes performing an averaging process to obtain at least one of said persisted signals as a weighted average of two or more of the Doppler information signals and/or the persisted signals and/or signals derived therefrom, employing said weighting factors that are functions of an energy related parameter of one or more Doppler information signals and/or the persisted signals and/or signals derived therefrom.

Still another aspect of the invention is directed to an ultrasound diagnostic imaging apparatus for imaging conditions of fluid flow or tissue motion within a body. The apparatus includes means for providing a first sequence of information signals containing Doppler or time shift information from the fluid flow or tissue motion; and means for producing from said first sequence of Doppler information signals a corresponding second time sequence of persisted signals. The producing means includes means for analyzing one or a combination of one or more information signals and/or persisted signals and/or signals derived therefrom to determine whether said information signals indicate types of information present in the information signals, said types including noise, low energy flow or tissue motion, high energy flow or tissue motion or flash, and means for selecting one or more weighting factors according to the type or types of information present. The producing step also includes performing an averaging process to obtain at least one of said persisted signals as a weighted average of two or more of the Doppler information signals and/or the persisted signals and/or signals derived therefrom, employing said weighting factors that are functions of an energy related parameter of one or more Doppler information signals and/or the persisted signals and/or signals derived therefrom.

BRIEF DESCRIPTION OF THE DRAWINGS

FIG. 1 is a block diagram of an ultrasound diagnostic imaging system for imaging a body to illustrate the invention.

FIG. 2A is a block diagram of an infinite impulse response (IIR) filter in the persistence accumulator of the color Doppler processor of FIG. 1 to illustrate the preferred embodiment of the invention.

FIG. 2B is a schematic circuit diagram illustrating an alternative embodiment of the thresholding and weighting part of the IIR filter shown in FIG. 2A.

FIG. 2C is a block diagram of a filter having feedforward and feedback paths in the persistence accumulator of the color Doppler processor of FIG. 1 to illustrate an alternative embodiment of the invention.

FIG. 3 is a block diagram of a finite impulse response filter in the persistence accumulator of FIG. 1 to illustrate another alternate embodiment of the invention.

FIG. 4A is a graphical illustration of a "flash" signal and a perfusion signal useful for illustrating the invention.

FIG. 4B is a graphical illustration of the "flash" and perfusion signals after conventional temporal persistence has been applied.

FIG. 4C is a graphical illustration of the "flash" and perfusion signals to illustrate the effects of the invention.

FIGS. 5, 6 and 7 are schematic circuit diagrams of a clipper circuit that may be used in the persistence accumulator of FIG. 1 to illustrate the preferred and alternative embodiments of the invention.

FIG. 8 is a block diagram of an ultrasound diagnostic imaging system acquiring time shift information and performing an averaging process or a clipping process to illustrate an alternative embodiment of the invention.

Identical components in this application are identified by the same numerals.

DETAILED DESCRIPTION OF THE PREFERRED EMBODIMENT

One aspect of the invention is based on the observation that by varying the amount of persistence as a function of the energy or strength of the Doppler signal, weak signals can be persisted longer than strong signals. This scheme improves the SNR for weak signals, but should a strong Doppler signal appear, it would not be persisted as long and good temporal resolution will be preserved. If a "flash" artifact occurs, since it would be a strong signal, it would not be persisted and would clear out of the image very quickly. This invention may be used for imaging fluid flow such as blood flow in a body, as well as for imaging tissue motion in the body.

FIG. 1 is a block diagram to illustrate the preferred embodiment of the invention. An ultrasound imaging system 10 includes a transmitter 12 controlled by a controller 14 to excite a transducer 16 which propagates ultrasonic bursts into a body (not shown) in a scan plane 18. The returning echoes are amplified and focused by means of the receiver/beamformer 20. Transducer 16 may propagate the ultrasonic bursts along different scan lines in the scan plane to scan a region of interest in the body to provide signals for color Doppler imaging. Alternatively, transducer 16 may propagate ultrasonic bursts along a single scan line in what is known as the M mode. In both cases, transducer 16 senses the echo from the body in response to the ultrasonic bursts, and a signal representative of the echo is amplified and focused by receiver/beamformer 20, downshifted to and filtered at its baseband by processor 22 and then digitized by converter 24. In both cases, converter 24 may produce P samples from sampling the returning echo caused by the propagation of one or more ultrasonic burst signals from transducer 16 into the body, therefore providing at the output of the converter an input sequence x(n) for the nth frame of length P (i.e. x(n) consisting of the sequence $x_p$ with p ranging from 0 to P−1) to the color Doppler processor 30. Processor 30 includes an autocorrelator 32 which computes the zeroth and first order autocorrelation coefficients of the input sequence x(n). The zeroth autocorrelation coefficient R(0) is a real number while the first autocorrelation coefficient R(1) is a complex number comprising a real and an imaginary part. For an input sequence x(n) of length P, the zeroth and first autocorrelation coefficients are defined by:

$$R(0) = \sum_{p=0}^{P-1} x_p * \overline{x_p}$$
$$R(1) = \sum_{p=1}^{P} x_p * \overline{x_{p-1}}$$

where $\overline{x_p}$, $\overline{x_{p-1}}$ are the complex conjugates of $x_p$, $x_{p-1}$.

The zeroth order correlation coefficient is used to derive energy information of the Doppler information signal x(n) while both the zero and first order coefficients are used for velocity and variance estimation. While in the embodiment described above, only the zeroth and first order autocorrelation and coefficients are used for energy, velocity and variance estimation, it will be understood that higher order correlation coefficients may be used as well for such estimation or estimation of other signal statistical characteristic estimation; such variations are within the scope of the invention.

The invention is applicable to at least two currently used color Doppler imaging modes: color Doppler velocity and variance imaging and color Doppler energy imaging. Aside from such currently used modes, the invention is also applicable to other modes as well. In either display mode, a clinical user is likely to encounter different types of color signals:

1. High energy flow signal (e.g., from arterial flow);
2. Low energy flow signal (e.g., from tissue perfusion or venous flow);
3. "Flash" artifacts (e.g., from transducer motions or patient motion); and
4. Low level system noise.

One aspect of the adaptive temporal integration or filtering of this invention is to use long temporal persistence for the low level perfusion signals to increase sensitivity but to "protect" or isolate the persistence accumulator or processor from regenerating (i.e., persisting) high energy signals such as "flash" artifacts or high velocity flow signals. This may be realized by analyzing the characteristics of the digitized signals from converter 24 or from auto-correlator 32 or calculator 36, classifying them as either noise, low energy flow signal, high energy flow signal or "flash," and then assigning different temporal integration coefficients according to the nature of the signal by means of a lookup table, such as in the scheme of FIG. 2B described below, for example. The adaptive temporal integration or filtering is performed by means of persistence accumulator 34. The analysis into the different types of information in the Doppler signals (or time shift signals as described below) and the assignment of integration coefficients or weighting factors may be performed by means of a lookup table stored in a programmable read-only-memory.

FIG. 2A is a schematic circuit diagram of persistence accumulator 34 of FIG. 1 useful to illustrate the preferred embodiment of the invention. As shown in FIG. 2A, the input signal x(n) to the accumulator is applied to an adder 50 which adds to the current value of x(n) a feedback value and provides the sum y(n) at the output of accumulator 34. If the current value x(n) is not the first digital sample of the input sequence, then there is a prior output y(n−1) for the (n−1)th frame provided by adder 50 during the immediately preceding frame time interval. Delay 52 delays the output of adder 50 during the preceding frame time interval so that the output y(n−1) for the prior sampling interval is present at the output of delay 52 when the current value x(n) is applied to adder 50. The energy value indicated by y(n−1) is compared to a threshold by comparator 54. If the energy value is above the threshold, comparator 54 enables path A in FIG. 2A so that multiplier 62 multiplies the value y(n−1) by a factor $a_{short}$ and provides the product to adder 50. If the energy value indicated by y(n−1) does not exceed the threshold, comparator 54 activates path B instead so that multiplier 64 multiplies y(n−1) by the factor $a_{long}$ and provides the product to adder 50 through line 66.

Thus, the threshold in comparator 54 is at such a level that when the energy indicated by y(n−1) exceeds the threshold, high energy flow signal or "flash" artifacts are indicated, so that a small persistence coefficient $a_{short}$ is applied in the temporal persistence applied by accumulator 34. If the energy value indicated by y(n−1) does not exceed such threshold, low energy flow signal and/or low level system noise is indicated and the comparator enables path B to heavily integrate or persist the signals in order to improve SNR by choosing a weighting factor $a_{along}$ much larger than $a_{short}$. Threshold comparator 54 may comprise a simple comparator and a switch. A suitable threshold to be used in comparator 54 is a value in a range of about half to 0.8 times the maximum value of the dynamic range of the Doppler information signal energy. Instead of comparing y(n−1) to the threshold, comparator 54 may also be moved to dotted line position 54a to compare $a_{short}*y(n-1)$ and $a_{long}*y(n-1)$ with threshold instead.

Accumulator 34 includes a memory (not shown) that stores the current averaged value for each location of the body that is interrogated. During the next frame time interval, the averaged value stored for a particular location of the body is replaced by the updated current value obtained by averaging the stored value and information in the current input sequence. Thus in the example above, the previous averaged value y(n−1) for the previous image frame stored in the memory is replaced by the current averaged value y(n)

for the current image frame. Thus the raw data x(n) is not stored. It will be obvious, however, that a separate frame buffer memory may be used to store the input sequence x(n).

It will be noted that the input signal x(n) and output signals y(n), y(n−1) are complex signals. If the input signal x(n) is taken from the autocorrelator 32 of FIG. 1, then the accumulator 34 would operate on the zeroth and real and imaginary parts of first order autocorrelation coefficients R(0), R(1), and so that each of x(n), y(n), y(n−1) will each consist of three components. Since the zeroth autocorrelation coefficients represents energy of the Doppler information in the echo received by receiver 20, comparator 54 compares the zeroth order autocorrelation coefficient of y(n−1) with the threshold.

In an alternative embodiment, persistence accumulator 34 may operate on the mean velocity , variance of velocity and energy estimated by calculator 36 instead of the autocorrelation values. In such alternative embodiment, the persistence accumulator 34 is removed in FIG. 1 from the signal path between the autocorrelator 32 and calculator 36 and placed between calculator 36 and color encoder 40, where the calculator 36 receives its input from autocorrelator 32. In such embodiment, calculator 36 would estimate from the zeroth and first order autocorrelation coefficients the mean velocity, variance of velocity, and energy of the Doppler shift information in the echo received by receiver 20. For a known method of such estimation, see "Real-Time Two-Dimensional Blood Flow Imaging Using an Autocorrelation Technique," by Kasai et al., *IEEE*, 1985. Persistence accumulator 34 then operates on such estimated mean velocity, variance of velocity, and energy to perform the adaptive temporal persistence. In such event, the input signal x(n), y(n) and y(n−1) would each have the following three components: mean velocity, variance of velocity, and energy. In such event, comparator 54 would compare the estimated energy with the threshold. In all of the embodiments described herein in reference to FIG. 1, the output parameter signals of the accumulator 34 are then color-encoded by color encoder 40, scan converted by color scan converter 42, and displayed on color monitor 44.

To acquire the nth frame of image of a particular region of the body, the transducer 16 transmits ultrasound pulses sequentially along scan lines across scan plane 18. The Doppler information on fluid flow or tissue motion at a location in the region present in the backscatter of a series of pulses from the location is processed and provided to the processor 30 as an input sequence x(n). This process is repeated for a sequence of frames, to acquire Doppler information on fluid flow or tissue motion at the same location in the region, resulting in a first time sequence of Doppler information signals x(n), with n indicating the nth signal in the time sequence for the nth frame. Accumulator 34 then computes a weighted average of the signal x(n) and the average value y(n−1) for the prior frame at the same location within the body. Accumulator 34 then provides an output y(n) as the weighted average for the nth frame corresponding to the input value x(n). The accumulator therefore provides from the first time sequence of Doppler information signals consisting of x(n) for different integer values of n corresponding to the successive frames taken, a corresponding second sequence of persisted (or parameter) signals y(n). Each Doppler information signal in the sequence contains Doppler information from fluid flow or tissue motion at a location within the body. Each signal in the second time sequence of persisted (or parameter) signals corresponds to a signal in the first time sequence, and relates to and contains information on the mean velocity of the fluid flow or tissue motion, variance of velocity of the fluid flow or tissue motion or energy of the Doppler information signals in the first sequence.

When accumulator 34 operates on the autocorrelation values from autocorrelator 32, the Doppler information signal x(n) at the input of the accumulator are the zeroth and first order autocorrelation coefficients, and the output of the accumulator y(n) will be the persisted values of these coefficients. Where the accumulator 34 operates on the estimated mean velocity of fluid flow or tissue motion, variance of velocity of fluid flow or tissue motion or energy of the Doppler information signals, the persisted (or parameter) signal y(n) at the output of the accumulator will be the persisted values of these quantities.

In some circumstances, it may be desirable to provide more than two weighting coefficients than as shown in FIG. 2A in the adaptive temporal averaging process performed by accumulator 34. In such event, the circuit within box 80 may be replaced by the circuit 90 of FIG. 2B. As shown in FIG. 2B, the delayed output y(n−1) for the prior sampling interval on line 53 is fed to a lookup table 92 and multiplier 94. Lookup table 92 then provides a weighting coefficient a to multiplier 94 which provides the product a*y(n−1) to line 66 and adder 50. In this manner, one of a number of weighting factors may be selected if the persisted or parameter signal y(n−1) of the last frame at the same location is within a corresponding range of values. If a large lookup table is chosen, the lookup table may be used as a good approximation for selecting weighting factors as a continuous function of y(n−1).

In reference to FIG. 2A, if path A is chosen, the following equation is implemented:

$$y(n)=x(n)+a_{short}*y(n-1)$$

If path B is chosen, then the following equation is implemented instead:

$$y(n)=x(n)+a_{long}*y(n-1)$$

In radiology applications, $a_{short}$ preferably has a value in the range of 0.125 to 0.25 and $a_{long}$ has a value in the range of 0.615 to 0.75, although respective broader ranges of 0 to 0.5 for $a_{short}$ and 0.25 to 0.8 for $a_{long}$ may also be used. For cardiology applications, the corresponding preferable range of values for $a_{short}$, $a_{long}$ are 0 to 0.125 and 0.125 to 0.25 respectively, although respective broader ranges of 0 to 0.25 for $a_{short}$ and 0.1 to 0.5 for $a_{long}$ may also be used.

The two embodiments of the persistence accumulator 34 in FIGS. 2A, 2B include feedback loops in a configuration known as infinite impulse response (IIR) filters. It will be evident that the values of more than one prior frame may be fed back, such as y(n−2), y(n−3), . . . The IIR filter may also include one or more feed forward signals such as x(n−1), x(n−2), which are the Doppler information signals in the time sequence provided by the transducer, receiver, base band processor, and analog digital converter for the frames prior to the nth frame. Such configuration is shown in FIG. 2C. As shown in FIG. 2C, threshold comparator 54' may be implemented as a lookup table stored in a programmable read-only-memory (PROM) or other types of memory to generate the multiplying factors $a_1, a_2, \ldots, c_1, c_2, \ldots$, to be applied as the multiplying factors to the multipliers 63 downstream from the comparators. The comparator 54' is thus somewhat different in structure from comparator 54 of FIG. 2A. The configuration of FIG. 2C can be used to arrive at any weighted combination of the signals x(n), x(n−1), x(n−2), . . . , y(n−1), y(n−2), . . . ,. Alternatively, comparators of the type shown and described in FIG. 2A may be used instead in FIG. 2C for comparators 54' and are within the scope of the invention. Thus, in general and according to FIG. 2C, the operation of the above-described general IIR filter may also be expressed mathematically in the following relation where y(n) is obtained by averaging over feedforward signals in M+1 frames and feedback accumulated signal values in N frames:

$$y(n) = \sum_{i=0}^{M} c_j x(n-i) + \sum_{j=1}^{N} a_j y(n-j)$$

where M is a non-negative integer, and N is a positive integer, x(n-i) are feed forward signals, y(n-j) are feedback signals, and $c_i$, $a_j$ are weighting factors. In the simplest cases, M is 0 and N is 1; or M is 1 and N is 0; or both M and N are 1. A finite impulse response (FIR) filter with only feedforward terms is possible and may be desirable in some situations since one can insure that large "flash" signals will be cleared out of the image within the number of frames equal to the number of feedforward terms implemented in the FIR filter. Such FIR filter is shown in FIG. 3. It will be noted that in FIG. 3, instead of using a threshold comparator to select a multiplying factor, a lookup table 54' is used which gives more flexibility to the system in choosing one of more than two weighting factors if desirable, each for a different range of energies of the input signal, for controlling the weighting of the feedforward signals.

Where in addition to the zeroth and first order correlation coefficients, higher order autocorrelation coefficients are used as well, comparator 54 in FIG. 2A may need to be replaced by a multi-dimensional threshold comparator. Alternatively, the lookup table 92 of FIG. 2B may be constructed to handle the higher order autocorrelation coefficients as well as the low order ones. In the embodiments described above, the same weighting factor is used for persisting mean velocity, variance of velocity, and energy. Obviously, different weighting factors may be chosen for the three variables instead; all such variations are within the scope of the invention. Adaptive temporal filtering may also be applied in color Doppler velocity and variance imaging as well as color Doppler energy imaging or other color imaging modes.

FIGS. 4A–4C illustrate the results achievable using the invention of this application. FIG. 4A is a graphical illustration of actual data of a flash signal and perfusion signals to illustrate the invention. As shown in FIG. 4A, 202 is a "flash" signal of large amplitude, such as caused by transducer motion and 204 are perfusion signals (or signals indicating tissue motion) of low amplitude that are received by receiver 20 of FIG. 1. Not shown in FIG. 4A is system noise which may be of essentially the same order of magnitude as the perfusion signals. It is therefore important to perform temporal averaging which adds the perfusion signals representing the fluid flow or tissue motion information at one location in the body with the perfusion signals representing fluid flow or tissue motion at the same location in the prior frames. Since the perfusion signals are slow changing and may be largely the same throughout a number of frames whereas system noise may be random, such temporal averaging would greatly enhance SNR.

Conventional persistence of the perfusion signals in the presence of "flash" signal 202, however, does not improve the SNR and may, in some circumstances, worsens it. This is shown, for example, in FIG. 4B. As shown in FIG. 4B, if the temporal averaging weighting factors are chosen appropriately for increasing SNR of the perfusion signals relative to system noise, and when such weighting factors are also applied to the "flash" signal, this has the effect of persisting the "flash" signal as well. Because of the large amplitude of the "flash" signal, the trailing portion of the "flash" signal overlaps and drowns a portion of the perfusion signal which is undesirable. As shown in FIG. 4B, the trailing edge of the "flash" signal lingers because of the effect of the IIR filter which persists the effect of such "flash" long after the "flash" signal in the actual data has passed.

FIG. 4C illustrates the effect of adaptive temporal averaging of this invention. Thus, when the "flash" signal is detected, comparator 54 or lookup table 92 would cause little or no temporal persistence to be applied by choosing a very small value for $a_{short}$. Then after the "flash" signal passes and perfusion signals or system noise is detected, comparator 54 would cause a large weighting factor $a_{long}$ to be applied to improve SNR, as shown in FIG. 4C. Even though not shown in FIG. 4C, it will be evident to those skilled in the art that adaptive temporal filtering described herein also enables dynamic temporal information and good temporal resolution of strong flow signals such as arterial flows to be retained while still enhancing SNR for perfusion type signals. Thus, when a strong flow signal is detected, comparator 54 or lookup table 92 would cause a low weighting factor $a_{short}$ to be chosen and the arterial flow would not appear sluggish. Upon the passage of such strong flow signals and the appearance of perfusion type signals (perfusion or tissue motion), a large weighting factor $a_{long}$ is chosen to increase SNR.

Instead of performing an averaging process in the adaptive temporal filtering in accumulator 34, a special clipping operation may be performed instead as illustrated in FIGS. 5–7. FIG. 5 is a schematic circuit diagram of accumulator 34 to illustrate an alternative embodiment of the invention. As shown in FIG. 5, the energy indicated by the current value x(n) is compared to a threshold in a clipper circuit 252 which compares the energy (e.g. R(0)) indicated by x(n) to a threshold. If such energy is greater than the threshold, then the clipper circuit provides to adder 50 an output value (e.g. R(0)) which would cause the energy to be substantially equal to the threshold. When the energy indicated by x(n) does not exceed the threshold, the clipper circuit 252 simply passes the input signal x(n) to adder 50. Delay circuit 52 again delays the output for the prior frame y(n−1) and supplies it to multiplier 254 which in turn multiplies such signal by a constant a and provides the product to adder 50. Adder 50 then adds the clipped input from clipper circuit 252 to this product to obtain the output y(n) of the accumulator 250. The clipped signal in the manner described above at the output of clipper circuit 252 is represented by ⌈x(n)⌋. Clipper circuit may be implemented as a programmable memory, such as a programmable read-only-memory or PROM. A suitable threshold to be used in clipper circuit 252 is a value in a range of about half to 0.8 times the maximum value of the dynamic range of the Doppler information signal energy.

FIG. 6 illustrates an alternative embodiment 260 for the accumulator 34 of FIG. 1. Instead of clipping the incoming signal as in FIG. 5, the clipper circuit 252 in FIG. 6 is placed at the output of adder 50 for clipping the output and such clipped output is fed to delay circuit 52 for deriving the output for the next frame, where the clipping function is the same as that described above in reference to FIG. 5. FIG. 7 illustrates yet another alternative embodiment where the clipper circuit 252 is placed between the delay circuit 52 and multiplier 254. Where the signals x(n), x(n−1), x(n−2), . . . , y(n−1), y(n−2), . . . are combined in a manner similar to that in FIG. 2C, a combination of such signals and/or signals derived therefrom may be obtained and clipped in clipper circuit 252 so that the value of the combination does not exceed a predetermined threshold.

The function of the clipper circuit 252 in FIGS. 5–7 limits the size of the flash artifact and blocks large signals from being accumulated or persisted. When the "flash" signal x(n) is encountered, for example, the circuit of FIG. 5 would clip it so that its energy is substantially equal to the threshold value so that the masking effect of the persisted "flash" signal on low velocity signals would be reduced. The circuit of FIG. 5 has the advantage of reducing immediately the effect of a rising edge of large "flash" signal. The circuits of FIGS. 6 and 7 have similar advantages even though they are not as effective in reducing the adverse effects of the rising edge of a large "flash" signal. The circuit of FIG. 7 is preferred over those of FIGS. 5 and 6, since the clipper circuit is not in the main signal path but only in the feedback path, so that the clipper circuit does not limit the dynamic range of the main signal path to the clipping threshold value while at the same time reducing the effect of "flash" on the accumulated or persisted signal.

A particularly advantageous configuration will be to combine FIGS. 2A and 7. Thus, if FIG. 2A is modified by including a clipper signal 252 at the output of delay circuit 52 to clip its output y(n–1) before it is applied to comparator 54, then the advantages of circuits in both FIGS. 2A and 7 would be available. This is indicated by the box 252 in dotted line in FIG. 2A. In other words, the clipper circuit 252 at the input of comparator would further reduce the adverse effect of the rising edge of a large "flash" signal while the averaging process performed by the remainder of the circuit in FIG. 2A would further ensure that the effect of the "flash" would be cleared out of the image fairly quickly. If it is desired to clip the input signal x(n) even though this will limit the dynamic range of the signal, the clipper circuit may also be placed at the input line to adder 50 in FIG. 2A.

The invention has been described at this point by operations of the persistence accumulator on Doppler information signals containing Doppler information. Essentially the same advantages can be obtained even if a somewhat different scheme is employed to derive the mean velocity, variance of velocity, and energy using time shift information instead of Doppler information. U.S. Pat. No. 4,928,698 describes a system employing time shift information for deriving the velocity and energy related to blood flows and motion of organs. FIG. 8 is a block diagram illustrating how the concept of this invention may be applied to perform adaptive temporal filtering based on time shift information in a system such as that described in U.S. Pat. No. 4,928,698 and the article "*Time Domain Formulation of Pulse Doppler Ultrasound and Blood Velocity Estimation by Cross-Correlation*," by Bonnefous et al., *Ultrasonic Imaging*, 8, 73–85 (1986). As shown in FIG. 8, the echoes received by receiver 20 are not down shifted to baseband as in FIG. 1 but simply converted to digital samples by converter 24 and cross-correlated by cross-correlator 302, which provides as its output energy and mean velocity of the fluid flow or tissue motion in the body. Persistence accumulator 34 then performs essentially the same operations of the type described above in reference to FIGS. 2A–7 to provide the different advantages described above. The output persisted (or parameter) signals of the accumulator are then color-encoded by color encoder 40, scan converted by color scan converter 42, and displayed at color monitor 44.

The invention has been described above by reference to different embodiments. It will be understood that various modifications and changes may be made without departing from the scope of the invention which is to be defined only by the appended claims. For example, in addition to choosing weighting factors as a function of energy, the weighting factors may also be chosen also as a function of mean velocity and/or variance of velocity information. While in the description above, the energy or zeroth order autocorrelation coefficient of one feedforward signal (x(n), x(n–1), . . . ) or one feedback signal (y(n–1), y(n–2), . . . ) is compared to a threshold in a comparator or clipper circuit, it will be understood that the energy or zeroth order autocorrelation coefficient of a combination of such signals or of such signals and/or signals derived therefrom may be used for comparison instead.

What is claimed is:

1. An ultrasound diagnostic imaging method for imaging conditions of fluid flow or tissue motion within a body, comprising the steps of:

providing a first time sequence of Doppler information signals containing Doppler information from the fluid flow or tissue motion; and producing from said first sequence of Doppler information signals a corresponding second time sequence of persisted signals;

wherein said producing step includes performing a temporal averaging process to obtain at least one of said persisted signals as a weighted average of two or more of the Doppler information signals and/or the persisted signals, employing weighting factors that are functions of an energy related parameter of at least one of one or more Doppler information signals and/or the persisted signals and/or signals derived therefrom.

2. The method of claim 1, further comprising displaying the persisted signals on a display medium.

3. The method of claim 1, wherein said performing step performs the averaging process to obtain the second sequence of persisted signals y(n) each corresponding to a Doppler information signal x(n) in said first sequence, n being a non-negative integer index for the sequences so that a Doppler information signal x(n) in the first sequence is the same as or is provided in the providing step after x(n-i), where i is a non-negative integer not greater than n, and so that y(n) is a persisted signal in the second sequence produced in the producing step after y(n-j), where j is a positive integer not greater than n, said performing step obtaining persisted signals y(n) from feedforward signals x(n-i) and feedback signals y(n-j) according to the relation below:

$$y(n) = \sum_{i=0}^{M} c_j x(n-i) + \sum_{j=1}^{N} a_j y(n-j)$$

where M is a non-negative integer, and N is a positive integer, and $c_i$, $a_j$ are weighting factors.

4. The method of claim 3, wherein M is zero or 1 and N is zero or 1.

5. The method of claim 3, said performing step performing an averaging process to obtain y(n) as a weighted average of x(n) and y(n–1).

6. The method of claim 5, said performing step including the steps of:

comparing y(n–1) or x(n) or a signal derived from y(n–1) or x(n) with a first threshold; and selecting one of two or more different weighting factors for the averaging process in response to the result of the comparison.

7. The method of claim 6, said performing step obtaining y(n) by computing according to one of the following two equations (1) and (2):

$$y(n)=x(n)+a_{short}*y(n-1) \quad (1)$$

$$y(n)=x(n)+a_{long}*y(n-1) \quad (2)$$

where $a_{short}$, $a_{long}$ are weighting factors, and $a_{long}$ being larger than $a_{short}$.

8. The method of claim 7, said selecting step selecting the weighting factor $a_{short}$ and equation (1) when y(n−1) exceeds said first threshold, and selecting the weighting factor $a_{long}$ and equation (2) when y(n−1) does not exceed said first threshold.

9. The method of claim 7, wherein $a_{short}$ is in the range of 0 to 0.5, and $a_{long}$ is in the range of 0.25 to 0.8.

10. The method of claim 7, wherein $a_{short}$ is in the range of 0 to 0.25, and $a_{long}$ is in the range of 0.1 to 0.5.

11. The method of claim 6, said performing step obtaining y(n) by computing according to one of the following two equations (1) and (2):

$$y(n)=[x(n)]+a_{short}*y(n-1) \quad (1)$$

$$y(n)=[x(n)]+a_{long}*y(n-1) \quad (2)$$

where $a_{short}$, $a_{long}$ are weighting factors, and $a_{long}$ being larger than $a_{short}$, and [x(n)] is the value of x(n) when such value does not exceed a predetermined second threshold and is equal to said second threshold when such value exceeds said second threshold.

12. The method of claim 11, said selecting step selecting the weighting factor $a_{short}$ and equation (1) when x(n) exceeds said first threshold, and selecting the weighting factor $a_{long}$ and equation (2) when x(n) does not exceed said first threshold.

13. The method of claim 3, said performing step including the steps of:

comparing the value of a combination of one or more of the feedforward and feedback signals in said relation with a threshold; and selecting weighting factors for the averaging process in response to the result of the comparison.

14. The method of claim 13, wherein said comparing step compares said value to thresholds stored in a lookup table, and said selecting step selects weighting factors as continuous or discrete functions of the value.

15. The method of claim 3, further comprising the step of clipping the value of a combination of one or more feedforward and feedback signals in said relation so that said value does not exceed a corresponding predetermined value.

16. The method of claim 15, wherein said clipping step clips the value of x(n), y(n−1) or a weighted average of x(n) and y(n−1).

17. The method of claim 1, wherein said weighting factors are also functions of either mean velocity of fluid flow at said location, or variance of fluid flow velocity at said location, or both.

18. The method of claim 1, said producing step including estimating from said first sequence of Doppler information signals the mean velocity, variance of velocity and energy related parameter of said Doppler information signals.

19. The method of claim 18, said producing step further including:

comparing the energy related parameter of said Doppler information signals or variance of velocity of the fluid flow to a threshold; and selecting a weighting factor in response to the comparison.

20. The method of claim 19, the energy related parameter of said Doppler information signals or signals derived therefrom having a dynamic range and a maximum value of said range, said comparing step comparing said energy related parameter to a threshold that is in a range of about half to 0.8 times the maximum value.

21. The method of claim 1, said producing step including sampling the Doppler information signals to obtain signal samples and autocorrelating said samples to obtain zeroth order and at least one higher order autocorrelation coefficient.

22. The method of claim 21, said producing step further including:

comparing the zeroth order autocorrelation coefficient to a threshold; and selecting a weighting factor in response to the comparison.

23. An ultrasound diagnostic imaging method for imaging conditions of fluid flow or tissue motion within a body, comprising the steps of:

providing a first sequence of Doppler information signals, each signal in the sequence containing Doppler information from the fluid flow or tissue motion; and producing from said first sequence of Doppler information signals a corresponding second sequence of persisted signals;

wherein said producing step includes the step of clipping the value of a combination of one or more Doppler information signals and/or the persisted signals so that said value does not exceed a non-zero predetermined value.

24. The method of claim 23, wherein said producing step includes the step of performing an averaging process to obtain at least one of said persisted signals in the second sequence as a weighted average of a combination of two or more of the Doppler information signals and/or persisted signals, employing weighting factors that are functions of the energy related parameter of said Doppler information signals and/or the persisted signals and/or signals derived therefrom.

25. The method of claim 24, wherein said performing step performs the averaging process to obtain the second sequence of persisted signals y(n) each corresponding to a Doppler information signal x(n) in said first sequence, n being a non-negative integer index for the sequences so that a Doppler information signal x(n) in the first sequence is the same as or is provided in the providing step after x(n−i), where i is a non-negative integer not greater than n, and so that y(n) is a persisted signal in the second sequence produced in the producing step after y(n−j), where j is a positive integer not greater than n, said performing step obtaining persisted signals y(n) from feedforward signals x(n−i) and feedback signals y(n−j) according to the relation below:

$$y(n) = \sum_{i=0}^{M} c_i x(n-i) + \sum_{j=1}^{N} a_j y(n-j)$$

where M is a non-negative integer, and N is a positive integer, and $c_i$, $a_j$ are weighting factors.

26. The method of claim 25, further comprising the step of clipping the value of a combination of one or more feedforward and feedback signals in said relation so that said value does not exceed a corresponding predetermined value.

27. The method of claim 26, wherein said clipping step clips the value of x(n), y(n−1) or a weighted average of x(n) and y(n−1).

28. The method of claim 27, wherein said performing step performs the averaging process according to:

$y(n)=x(n)+a*y(n-1)$ and wherein the clipping steps clips the value of y(n) so that it does not exceed a predetermined value.

29. The method of claim 24, wherein said clipping step is carried out prior to, during or after said averaging process.

30. The method of claim 23, said clipping step including:
   comparing the value of said combination to a threshold value; and
   setting the value of said combination to said threshold value when such value exceeds the threshold value.

31. The method of claim 30, said Doppler information signals or signals derived therefrom having a dynamic range and a maximum value of said range, said comparing step comparing an energy related parameter of the Doppler information signals or signals derived therefrom to a threshold that is in a range of about half to 0.8 times the maximum value.

32. An ultrasound diagnostic imaging method for imaging conditions of fluid flow or tissue motion within a body, comprising the steps of:
   providing a first sequence of information signals, each signal in the sequence containing time shift information from the fluid flow or tissue motion; and
   producing from said first sequence of information signals a corresponding second sequence;
   wherein said producing step includes performing an averaging process to obtain at least one of said persisted signals as a weighted average of two or more of the information signals and/or the persisted signals, employing weighting factors that are functions of an energy related parameter of one or more information signals and/or the persisted signals and/or signals derived therefrom.

33. An ultrasound diagnostic imaging method for imaging conditions of fluid flow or tissue motion within a body, comprising the steps of:
   providing a first sequence of information signals, each signal in the sequence containing time shift information from the fluid flow or tissue motion; and
   producing from said first sequence of information signals a corresponding second sequence of persisted signals;
   wherein said producing step includes the step of clipping the value of a combination of one or more information signals and/or the persisted signals so that said value does not exceed a non-zero predetermined value.

34. An ultrasound diagnostic imaging apparatus for imaging conditions of fluid flow or tissue motion within a body, comprising:
   means for providing a first sequence of Doppler information signals, each signal in the sequence containing Doppler information from the fluid flow or tissue motion; and
   means for producing from said first sequence of Doppler information signals a corresponding second sequence of persisted signals;
   wherein said producing means includes means for performing an averaging process to obtain at least one of said persisted signals as a weighted average of two or more of the Doppler information signals and/or the persisted signals, employing weighting factors that are functions of an energy related parameter of at least one of one or more Doppler information signals and/or the persisted signals and/or signals derived therefrom.

35. The apparatus of claim 34, further comprising means for displaying the persisted signals on a display medium.

36. The apparatus of claim 34, said producing means including a color Doppler processor, wherein said processor comprises a persistence accumulator that performs the averaging process.

37. The apparatus of claim 36, said processor further comprising an auto-correlator that auto-correlates each Doppler information signal to provide auto-correlation functions, said persistence accumulator operating on said auto-correlation functions to perform the averaging process.

38. The apparatus of claim 36, said processor further comprising:
   an auto-correlator that auto-correlates each Doppler information signal to provide auto-correlation functions; and
   a calculator calculating the mean velocity, variance of velocity and energy of the Doppler information signals from the auto-correlation functions, said persistence accumulator operating on the mean velocity, variance of velocity and energy of the Doppler information signals from the calculator to perform the averaging process.

39. The apparatus of claim 36, said persistence accumulator including FIR and/or IIR filters.

40. The apparatus of claim 39, said persistence accumulator including an IIR filter, said filter including a forward path between an input and an output, said forward path including an adder, and a feedback path including:
   means for delaying the output;
   a comparator for comparing the delayed output to a threshold;
   two parallel sub-paths each including a multiplier for multiplying the output of the comparator with a constant and providing the product signal to the adder, wherein one sub-path is enabled when the delayed output is above the threshold and the other sub-path is enabled when the delayed output is below the threshold.

41. The apparatus of claim 36, said persistence accumulator including at least one programmable memory for performing a clipping function, wherein an input signal is passed to an output of the memory when its amplitude is below a threshold value, and the output is set to the threshold value when the input signal amplitude is above the threshold value.

42. An ultrasound diagnostic imaging apparatus for imaging conditions of fluid flow or tissue motion within a body, comprising:
   means for providing a first sequence of Doppler information signals, each signal in the sequence containing Doppler information from the fluid flow or tissue motion; and
   means for producing from said first sequence of Doppler information signals a corresponding second sequence of persisted signals;
   wherein said producing means includes means for clipping the value of a combination of one or more of the Doppler information signals and/or the persisted signals and/or signals derived therefrom so that the value does not exceed a non-zero predetermined value.

43. The apparatus of claim 42, said producing means including a color Doppler processor, wherein said processor comprises a persistence accumulator that performs the averaging process.

44. The apparatus of claim 43, said processor further comprising an auto-correlator that auto-correlates each Doppler information signal to provide auto-correlation functions, said persistence accumulator operating on said auto-correlation functions to perform the averaging process.

46. The apparatus of claim 43, said processor further comprising:
   an auto-correlator that auto-correlates each Doppler information signal to provide auto-correlation functions; and
   a calculator calculating the mean velocity, variance of velocity and energy of the Doppler information signals from the auto-correlation functions, said persistence accumulator operating on the the mean velocity, variance of velocity and energy of the Doppler information signals from the calculator to perform the averaging process.

46. The apparatus of claim 43, said persistence accumulator including at least one lookup table for performing a clipping function, wherein an input signal is passed to an output of the lookup table when its amplitude is below a threshold value, and the output is set to the threshold value when the input signal amplitude is above the threshold value.

47. An ultrasound diagnostic imaging apparatus for imaging conditions of fluid flow or tissue motion within a body, comprising:
   means for providing a first sequence of information signals, each signal in the sequence containing time shift information from the fluid flow or tissue motion; and
   means for producing from said first sequence of information signals a corresponding second sequence of persisted signals;
   wherein said producing means includes means for performing an averaging process to obtain at least one of said persisted signals as a weighted average of two or more of the information signals and/or the persisted signals, employing weighting factors that are functions of an energy related parameter of one or more information signals and/or persisted signals and/or signals derived therefrom.

48. An ultrasound diagnostic imaging apparatus for imaging conditions of fluid flow or tissue motion within a body, comprising:
   means for providing a first sequence of information signals, each signal in the sequence containing time shift information from the fluid flow or tissue motion; and
   means for producing from said first sequence of information signals a corresponding second sequence of persisted signals;
   wherein said producing means includes means for clipping the value of a combination of one or more information signals and/or the persisted signals and/or signals derived therefrom so that the value does not exceed a non-zero predetermined value.

49. An ultrasound diagnostic imaging method for imaging conditions of fluid flow or tissue motion within a body, comprising the steps of:
   providing a first sequence of information signals containing Doppler or time shift information from the fluid flow or tissue motion; and
   producing from said first sequence of Doppler or time shift information signals a corresponding second time sequence of persisted signals;
   wherein said producing step includes:
      analyzing one or a combination of one or more information signals and/or persisted signals and/or signals derived therefrom to determine whether said information signals indicate types of information present in the information signals, said types including noise, low energy flow or tissue motion, high energy flow or tissue motion or flash, and selecting one or more weighting factors according to the type or types of information present; and
      performing an averaging process to obtain at least one of said persisted signals as a weighted average of two or more of the Doppler information or time shift information signals and/or the persisted signals and/or signals derived therefrom, employing said weighting factors that are functions of an energy related parameter of at least one of one or more Doppler information or time shift information signals and/or the persisted signals and/or signals derived therefrom.

50. An ultrasound diagnostic imaging apparatus for imaging conditions of fluid flow or tissue motion within a body, comprising:
   means for providing a first sequence of information signals containing Doppler or time shift information from the fluid flow or tissue motion; and
   means for producing from said first sequence of Doppler or time shift information signals a corresponding second time sequence of persisted signals;
   wherein said producing means includes:
      means for analyzing one or a combination of one or more information signals and/or persisted signals and/or signals derived therefrom to determine whether said information signals indicate types of information present in the information signals, said types including noise, low energy flow or tissue motion, high energy flow or tissue motion or flash, and for selecting one or more weighting factors according to the type or types of information present; and
      means for performing an averaging process to obtain at least one of said persisted signals as a weighted average of two or more of the Doppler information or time shift information signals and/or the persisted signals and/or signals derived therefrom, employing said weighting factors that are functions of an energy related parameter of at least one of one or more Doppler information or time shift information signals and/or the persisted signals and/or signals derived therefrom.

* * * * *

UNITED STATES PATENT AND TRADEMARK OFFICE
CERTIFICATE OF CORRECTION

PATENT NO. : 5,899,864
DATED : May 4, 1999
INVENTOR(S) : James W. Arenson et al.   Page 1 of 2

It is certified that error appears in the above-identified patent and that said Letters Patent is hereby corrected as shown below:

<u>On the Title Page</u>

In column 1, line 4, under "U.S. PATENT DOCUMENTS", change "Bonnefons" to --Bonnefous--.

In column 1, line 14, under "U.S. PATENT DOCUMENTS", change "Hall" to --Challa--.

In column 2, line 1, under "OTHER PUBLICATIONS", change "Real-Time" to --"Real-Time--.

In column 2, line 2, under "OTHER PUBLICATIONS", change "Technique," to --Technique",--.

In column 2, line 8, under "OTHER PUBLICATIONS", change "VTS" to --UTS-- and change "73-75" to --pp. 73-75--.

In column 2, line 10, under "OTHER PUBLICATIONS", change "Simulation" to --"Simulation--.

In column 2, line 11, under "OTHER PUBLICATIONS", change "Systems" to --Systems"-- and change "252-271" to --pp. 252-271--.

In column 3, line 36, change "$v = f_D * c / 2 f_0 * \cos\theta$" to --$v = f_D * c / 2 f_0 * \cos\theta$--.

UNITED STATES PATENT AND TRADEMARK OFFICE
CERTIFICATE OF CORRECTION

PATENT NO. : 5,899,864
DATED : May 4, 1999
INVENTOR(S) : James W. Arenson et al.

It is certified that error appears in the above-identified patent and that said Letters Patent is hereby corrected as shown below:

In column 10, line 54, change "x(n-2)," to --x(n-2), ...,--.

In column 11, in the equation, change "j" (first occurrence) to --i--.

In column 12, line 50, change "$\lceil x(n) \rfloor$" to --$\lceil x(n) \rceil$--.

In the Claims

In claim 3, in the equation, change "j" (first occurrence) to --i--.

In claim 32, line 14, change "of one" to --of at least one of one--.

In claim 47, line 16, change "of one" to --of at least one of one--.

Signed and Sealed this

Fifteenth Day of August, 2000

Attest:

Q. TODD DICKINSON

*Attesting Officer*  *Director of Patents and Trademarks*